United States Patent
Johns et al.

(10) Patent No.: US 9,545,224 B2
(45) Date of Patent: Jan. 17, 2017

(54) FITNESS FOR WORK TEST

(75) Inventors: Murray Johns, Richmond (AU); Andrew Tucker, Richmond (AU)

(73) Assignee: OPTALERT AUSTRALIA PTY LTD, Richmond, Victoria (AU)

(*) Notice: Subject to any disclaimer, the term of this patent is extended or adjusted under 35 U.S.C. 154(b) by 0 days.

(21) Appl. No.: 13/883,330

(22) PCT Filed: Nov. 7, 2011

(86) PCT No.: PCT/AU2011/001420
§ 371 (c)(1),
(2), (4) Date: May 3, 2013

(87) PCT Pub. No.: WO2012/061871
PCT Pub. Date: May 18, 2012

(65) Prior Publication Data
US 2013/0215390 A1    Aug. 22, 2013

(30) Foreign Application Priority Data
Nov. 8, 2010 (AU) .................. 2010904936

(51) Int. Cl.
*A61B 3/14* (2006.01)
*A61B 5/16* (2006.01)
(Continued)

(52) U.S. Cl.
CPC ............ *A61B 5/162* (2013.01); *A61B 3/113* (2013.01); *A61B 5/18* (2013.01)

(58) Field of Classification Search
CPC ............ A61B 5/1114; A61B 2017/00216; A61B 2503/22; A61B 5/16; A61B 3/113; A61B 5/0476; G02B 27/0093; G08B 21/06; G08B 23/00; B60K 28/06; G06K 9/00597; B60R 25/255; G02C 7/04; G02C 7/081; G06F 3/013
(Continued)

(56) References Cited

U.S. PATENT DOCUMENTS 5,137,345 A    8/1992 Waldorf et al.
5,311,877 A *  5/1994 Kishi .................. 600/545
(Continued)

FOREIGN PATENT DOCUMENTS

WO    WO-99/12137 A1    3/1999
WO    WO-03039358 A1    5/2003
(Continued)

*Primary Examiner* — Bumsuk Won
*Assistant Examiner* — Collin X Beatty
(74) *Attorney, Agent, or Firm* — Polsinelli PC (57) ABSTRACT

A system for measuring fitness for duty which includes a) a visual stimulus display b) eye monitoring equipment for measuring eye and eyelid movements c) a central processing unit and data storage device to collect and store the data from the eye monitoring equipment d) a data analysis device programmed to calculate one or more of the measures of blink latency, measures of the relative velocity of upper eyelid closing and opening movements during blinks, the product of the amplitude to velocity ratio of eyelid closing and opening, the duration of blinks, the variability of eyelid movements during blinks, the failure to respond appropriately with a voluntary blink following each said brief visual stimulus e) said data analysis device programmed to place the values for said measures into an algorithm for measuring fitness for duty.

9 Claims, 5 Drawing Sheets

(51) Int. Cl.
*A61B 3/113* (2006.01)
*A61B 5/18* (2006.01)

(58) Field of Classification Search
USPC .......... 340/575, 576; 600/558, 301; 348/78;
351/246; 434/236
See application file for complete search history.

(56) References Cited

U.S. PATENT DOCUMENTS

| | | | |
|---|---|---|---|
| 5,422,690 A * | 6/1995 | Rothberg et al. | 351/209 |
| 5,570,698 A * | 11/1996 | Liang et al. | 600/558 |
| 5,795,306 A * | 8/1998 | Shimotani et al. | 600/558 |
| 6,304,187 B1 * | 10/2001 | Pirim | 340/576 |
| 7,071,831 B2 | 7/2006 | Johns | |
| 7,344,251 B2 * | 3/2008 | Marshall | 351/246 |
| 7,380,938 B2 | 6/2008 | Chmielewski, Jr. et al. | |
| 7,438,418 B2 | 10/2008 | Marshall | |
| 7,682,024 B2 | 3/2010 | Plant et al. | |
| 7,791,491 B2 | 9/2010 | Johns | |
| 2004/0233061 A1 * | 11/2004 | Johns | 340/575 |
| 2008/0150734 A1 * | 6/2008 | Johns | 340/575 |
| 2008/0231461 A1 * | 9/2008 | Sanchez et al. | 340/575 |
| 2009/0123031 A1 * | 5/2009 | Smith et al. | 382/104 |
| 2009/0171240 A1 * | 7/2009 | Aguilar et al. | 600/558 |
| 2009/0184828 A1 * | 7/2009 | Speller | 340/575 |
| 2009/0261979 A1 * | 10/2009 | Breed et al. | 340/576 |
| 2009/0299209 A1 * | 12/2009 | Farbos | 600/544 |
| 2010/0214105 A1 * | 8/2010 | Manotas, Jr. | 340/575 |
| 2010/0238034 A1 * | 9/2010 | Gunaratne | 340/575 |
| 2010/0245093 A1 * | 9/2010 | Kobetski et al. | 340/576 |
| 2010/0253526 A1 * | 10/2010 | Szczerba et al. | 340/576 |
| 2011/0006903 A1 * | 1/2011 | Niem | 340/576 |
| 2011/0121976 A1 * | 5/2011 | Johns et al. | 340/576 |
| 2012/0077160 A1 * | 3/2012 | DeGutis et al. | 434/236 |
| 2012/0078115 A1 * | 3/2012 | Lonky | 600/476 |
| 2012/0169503 A1 * | 7/2012 | Wu et al. | 340/575 |
| 2012/0188355 A1 * | 7/2012 | Omi et al. | 348/78 |
| 2013/0012787 A1 * | 1/2013 | Horseman | 600/301 |
| 2013/0012832 A1 * | 1/2013 | Zelinsky | 600/558 |
| 2013/0044000 A1 * | 2/2013 | Nakai et al. | 340/575 |
| 2013/0090569 A1 * | 4/2013 | Jones et al. | 600/558 |

FOREIGN PATENT DOCUMENTS

| | | |
|---|---|---|
| WO | WO-2007016739 A1 | 2/2007 |
| WO | WO-2008107832 A1 | 9/2008 |
| WO | WO-2010006370 A1 | 1/2010 |

\* cited by examiner

FITNESS FOR WORK TEST

PRIORITY

Priority is claimed as a national stage application, under 35 U.S.C. §371, to PCT/AU2011/001420, filed Nov. 7, 2011, which claims priority to Australian Application No. 2010904936, filed Nov. 8, 2010. Each disclosure of the aforementioned priority applications is incorporated herein by reference in its entirety.

BACKGROUND

Field of the Invention

This invention relates to a method of testing for workers fitness to carry out allotted tasks particularly for vehicle or machine operators or other sedentary workers.

BACKGROUND TO THE INVENTION

There are many factors that can impair perception, cognition, memory and psychomotor performance in a way that makes a person unfit to carry out a task effectively and safely at the time. These factors include sleep deprivation, sleep disorders such as obstructive sleep apnea, traumatic brain injury and other acute illnesses that affect brain function, and the effects of alcohol and psychotropic drugs, whether used legally or not. The nature of such impairment depends to some extent on its cause. For example, the performance impairment associated with sleep deprivation is mainly caused by drowsiness, whereas alcohol causes other changes in brain function in addition to drowsiness. This impairment is also partially task-specific.

Most current attempts in industry to measure fitness for duty focus on the assessment of blood alcohol and either urinary or salivary drug testing. Such assessments are considered too cumbersome and too expensive to be used frequently, particularly on a daily basis.

There are existing technologies and methods that purport to measure fitness for duty, in a broader sense, based on ocular measurements. Most rely on pupillography, measuring the size of the pupil and its tendency to fluctuate in drowsy subjects when measured low-light conditions (Kristjansson S D, Stem J A, and Brown J W, *Detecting phasic lapses in alertness using pupillometric measures. Applied Ergonomics,* 2009; 40: 978-986.)

The response of the pupil to an intense flash of light is also often measured by the latency before its constriction begins and the velocity of that constriction.

Some technologies also measure the velocity of saccadic movements of the eyes, based on the time taken to move the eyes a known angular distance from one point to another (Rowland L M, Thomas M L, Thorne D R, Sing H C, Krichmar J L, Davis H Q, Balwinski S M, Peters R D, Kloeppel-Wagner E, Redmond D P, Alicandri E, and Belenky G. *Oculomotor responses during partial and total sleep deprivation. Aviation, Space and Environmental Medicine,* 2005; 76: C104-113). While these ocular measurements are effected by drowsiness induced by sleep deprivation and by sedative drugs, their effect size is small. For example, the saccadic velocity is reduced by only about 3% after 24 hours without sleep.

The validity and accuracy of such methods for assessing fitness for duty have been seriously questioned (Watson A, Miller L, Dawkins M, Lorenz C and Latman N S. *Evaluation of validity of the PMI FIT 2000-3 Fitness-for-Duty/Impairment screener. Journal of Clinical Engineering* 2006; 31: 206-212.).

U.S. Pat. No. 5,422,690 discloses a self screening test using variable light stimuli. Pupil dilation and eye tracking in following a moving light are measured. The pupil diameter and saccadic movement data are compared to baseline data for the same subject.

U.S. Pat. Nos. 7,344,251 and 7,438,418 disclose a method of determining mental proficiency by measuring point of gaze pupillary movement as a subject performs a task.

U.S. Pat. No. 7,380,938 discloses a two camera system for tracking eye movement in response to light stimuli. The system stores prior results for the individual and this can be used to assess fitness.

U.S. Pat. No. 7,682,024 discloses a saccadic motion detector that uses an optical navigation chip to record saccadic movements.

WO 2003/039358 and WO2007/016739 by one of the current inventors disclose a method and spectacles for the detection of drowsiness.

It is an object of this invention to provide a test of fitness for duty that is intended to be used as a brief test of brain function and psychomotor performance at a particular time that would indicate whether or not a person was fit from that point of view to begin a particular task or period of work, or having started it already, was fit to continue with it.

BRIEF DESCRIPTION OF THE INVENTION

To this end this invention provides a method of measuring fitness for duty which monitors voluntary blinks in response to brief visual stimuli in which the fitness for duty is measured using an algorithm that includes two or more of measures of blink latency, measures of the relative velocity of upper eyelid closing and opening movements during blinks, the product of the amplitude to velocity ratio of eyelid closing and opening movements, the duration of blinks, variability of eyelid movements during blinks, the failure to respond appropriately to the brief visual stimulus by making a voluntary blink.

The test of this invention differs from the prior art in that it tests neuro muscular function, especially in relation to eyelid movements as well as cognitive function. The impairment demonstrated by the test of fitness for duty according to this invention, applies to almost any task that requires attention and psychomotor skills, in particular to driving a vehicle of some kind, or tasks involving the monitoring or other use of industrial equipment.

In another aspect this invention provides a system for measuring fitness for duty which includes
  a) a visual stimulus display
  b) eye monitoring equipment for measuring eye and eyelid movements
  c) a central processing unit and data storage device to collect and store the data from the eye monitoring equipment
  d) of blink latency, measures of the relative velocity of upper eyelid closing and opening movements during blinks, the product of the amplitude to velocity ratio of eyelid closing and opening movements, the duration of blinks, the variability of eyelid movements during blinks, the failure to respond appropriately with a voluntary blink, following said brief visual stimuli
  e) said data analysis device programmed to place the values for said measures into an algorithm for measuring fitness for duty.

The following list ranks the variables used in the algorithm in approximate order of importance
a) Mean Amplitude Velocity Ratio (AVR) of Eyelid Closure
b) Standard Deviation Amplitude Velocity Ratio (AVR) of Eyelid Closure
c) Mean Amplitude Velocity Ratio (AVR) of Eyelid Reopening
d) Standard Deviation Amplitude Velocity Ratio (AVR) of Eyelid Reopening
e) Mean Product of AVRs (Eyelid Closure×Eyelid Reopening)
f) Standard Deviation Product of AVRs (Eyelid Closure× Eyelid Reopening)
g) Mean Blink Latency
h) Standard Deviation Blink Latency
i) Percent Errors of Omission
j) Percent Errors of Comission
k) Percent Total Errors (Sum of Errors of Omission and Comission)
l) Mean Blink Inter-Event Duration (time between maximum velocities of eyelid closure and eyelid reopening for each blink)
m) Standard Deviation Blink Inter-Event Duration (time between maximum velocities of eyelid closure and eyelid reopening for each blink)
n) Mean Total Blink Duration
o) Standard Deviation Total Blink Duration
p) Mean Eyelid Closure Duration
q) Standard Deviation Eyelid Closure Duration
r) the difference between a pair of percentiles for each variable (preferably $10^{th}$ and $90^{th}$ percentiles).

Algorithms using these variables are adapted to predicting impairment for duty due to sleep deprivation, consumption of alcohol, various drugs including cannabis and sedatives such as benzodiazepines, and acute brain injury or illness.

DETAILED DESCRIPTION OF THE INVENTION

The invention will now be described with reference to a preferred embodiment of the invention.

The main characteristics of eye and eyelid movement that are included in the algorithm of this invention are:
1. Blink latency: the interval between the onset of a stimulus and the initiation of eyelid closure during a blink made voluntarily as quickly as possible in response to the stimulus. Blink latencies are measured for a series of such blinks made in response to a brief visual stimulus repeated a number of times (typically about 30-50 times) at pseudorandom intervals varying between about 1 and 3 seconds. This test is equivalent to the more usual manual reaction-time test in which a button is pushed in response to the visual stimulus. However, the voluntary initiation of a blink as the response test avoids the complicating factors involved with greater distances of nerve conduction and the movement of bones and joints that are inherent in any manual response. Eyelid movements during blinks have no such limitations. Blink latencies are generally shorter than manual reaction times in response to the same stimulus. The measures of blink latency that best discriminate between people who are fit from those that are not include the percentage of a person's blink latencies that are longer than 95% preferably more than 97.5% (or the mean+2 standard deviations) of the latencies measured in people who are otherwise deemed to be fit.
2. Relative velocity of upper eyelid movements during blinks: The eyelid movements during blinks are under reflex controls whether the blinks are initiated voluntarily or spontaneously. The maximum velocity with which the upper eyelids close during blinks is linearly related to the amplitude of that movement. The further the lids have to move, the faster they do so. This relationship has been called the main sequence. There is a different main sequence for eyelids reopening during blinks. These relationships are controlled very closely by the brain in alert subjects, but those controls are loosened and intermittently fail in the drowsy state or with drugs that affect brain function.
In U.S. Pat. No. 7,071,831 the present inventor has described how the ratio of amplitude to maximum velocity (AVR) can be measured for eyelids closing and reopening during blinks as measures of alertness and brain function. Those ratios are also used here as a measure of the inhibition of neuromuscular function that characterizes drowsiness and many forms of brain dysfunction that impairs performance. The only difference with this new test is that the blinks are made voluntarily rather than spontaneously.
3. Product of AVRs for Eyelids Closing and Reopening During Blinks The AVR for eyelids closing is moderately correlated with the AVR for reopening within the same blinks. They must share some aspects of their controls (which are not well understood), but are also somewhat independent of each other. Both tend to increase with drowsiness, but not necessarily at the same time or equally in everyone. The product of these AVRs allows for such differences, so the mean of this product and its standard deviation per unit time are calculated as separate variables.
4. Duration of blinks: The total duration of each blink reflects the combined effects of several reflexes that control how long it takes the eyelids to close, how long they remain closed (normally only about 1 millisecond), and how long it takes them to reopen. These components of each blink can be measured separately, but often not very accurately, because it can be difficult to determine when each component begins and ends. This problem is ameliorated by measuring the interval between the time of maximum closing velocity and the subsequent time of maximum reopening velocity for the same blink. These are easily defined and measured from the velocity signal. This methodology has previously been described in the inventor's earlier patents, especially U.S. Pat. No. 7,791,491.
5. Variability of eyelid movements during blinks: We measure the mean values for each of the above variables recorded during the test of this invention, as well as their standard deviation as a measure of their variability during the test period.
6. Errors of omission: Failure to blink within a predetermined interval preferably 1 to 2 sec after the start of a visual stimulus represents an error of omission, ie failure to respond. Such errors rarely occur in people who are fit for duty. Errors of omission increase progressively with the duration of testing, which in this case is only about 1.5 minutes. However, they can also be caused by distraction during the test.
This can be limited by careful test procedures that prevent extraneous stimuli, such as loud noises or interruptions by people. An error of omission caused by distraction would be identified by its lack of association with other changes that would indicate impairment.

7. Errors of commission: blinks at inappropriate times, made in anticipation of, rather than as a response to, a stimulus.
8. Difference in percentiles Another measure of such variability would be the difference between pairs of percentiles for each variable. The $10^{th}$ and $90^{th}$ percentiles for each variable are preferred. This variability provides another source of information, in addition to that provided by mean values and standard deviations.

How these Variables are Measured

The measurements of eyelid movements that are used in the new test of fitness for duty could be made in several ways, including recordings of the electrooculogram from electrodes attached to the face, high-speed video camera images of the eyes, or infrared reflectance oculography. The latter is the method of choice, which could have at least two different manifestations. The first uses special glasses, as with the system according to patents WO 2003/039358 and WO2007/016739 that require initial fitment to each subject by someone trained in the art so that the infrared emitter and receiver are both placed in the appropriate places in relation to the eyes. A second, and preferred method would use infrared emitter(s) and sensor(s) fixed around a viewing device into which the test subject would look while performing the test. The subject would align the device to the appropriate position in front of one or other pupil, or both pupils, in which position a small "target" light would become visible to the subject. They would be asked to maintain that position and their view of the "target" light continuously for the duration of the test (about one or two minutes). The stimulus might then be the light being switched off for a brief period. Alternatively, the visual stimulus may be provided by another diffuse light (probably of a different colour) coming on in their visual field and clearly visible without the need for any eye movements. This stimulus would be on for only a brief period (of the order of 100-400 milliseconds) at random intervals between about 1.5 and 3 seconds. This method would eliminate the requirement for glasses and for their individual fitment by someone else.

Analysis of Recorded Data

Because this new test of fitness for duty is a one-off test each time it is used and also because it is such a brief test, the processing of recorded data can wait until after the test has ended, ie. analysis is performed off-line. This involves the retrospective determination of what a blink is during each test from its relative amplitude, duration and velocity. The calculated variables are then used either individually or in some combination to compare the current results with those previously recorded from the same subject. The differences between subjects (subject-specific differences) can thereby be eliminated. This makes the test far more sensitive to minor changes in fitness for duty for those subjects. Alternatively, the present results can be compared with those previously recorded from a whole population of other subjects. Even though the latter comparisons will be less sensitive than the former, they will still indicate which subjects are severely impaired at the time.

Errors of omission and commission are hallmarks of someone who is unfit for duty. If a person cannot maintain visual vigilance for one or two minutes, in the absence of external distractions, they are very unlikely to be able to perform most tasks required of them, effectively and safely over a period of hours. However, such errors are also associated with longer and more variable blink latencies, higher amplitude/velocity ratios for eyelids closing and reopening, and longer and more variable blink durations. The latter changes occur from the beginning of a test period, even periods as short as one minute, when errors of omission are unlikely to occur unless the subject is severely impaired. Thus, the associated changes can be seen as the portent of errors of omission, and indicators of some degree of impairment, even in the absence of errors of omission and commission.

These variables are usually correlated with one another significantly, but each also contributes unique information in its own right. They cover aspects of brain function that are predominantly tests of perception, cognition, short-term memory, the maintenance of visual attention and vigilance on the one hand, combined with tests of the reflex control of neuromuscular function on the other hand. This combination of variables has not been used previously in any other test of fitness for duty.

The subject's fitness for duty would be determined by one, or more likely, some combination of data recorded at the time and processed immediately afterwards, automatically. The final results could be displayed in several ways and also stored for later use. The results of each test could be displayed visually as the words "Pass", "Fail" or "Uncertain", with a distinguishing coloured light coming on. In addition, each test could be rated by a single percentage number (0 to 100%), referring to a direct comparison with that subject's previously recorded best results and/or the results from a comparable population sample.

Identification of the Test-Subject and Storage of Previous Results

Within the context of a one-off test of fitness for duty performed repeatedly on a particular subject there is a need to identify the subject uniquely each time the test is performed. This could be achieved by a memory device, such as a small memory stick, that stored identifiers and previously recorded results from that same subject who would carry the memory device. The testing device/procedure could include a finger-print reader, the output from which was compared with previously recorded finger-print information that uniquely identified that subject. In addition, the memory device could store the subject's best results (ie when he/she was most fit for duty) previously recorded with the same test battery, but not necessarily with the same piece of equipment. This could involve the storage of raw data for several variables, such as the blink latencies for each of 30-50 responses, or a summary of those data in terms of means and standard deviations, as well the time of day/night and the date of those results, and the name of the employer, etc.

The storage device would be necessary for tests with this new device to be performed repeatedly. Its use would increase the sensitivity of those tests by removing the differences between subjects. However, this would presumably not apply to tests that were not expected to be repeated, as with the one-off collection of results for law enforcement purposes. Those results could be compared only with data collected from a comparable population of subjects (eg with respect to the subject's age, and the time of day when the test was performed).

Features of the New Test of Fitness for Duty

The new test measures several variables and different aspects of performance because impairment that will increase the risk of performance failure is not a single entity, with the same manifestations in everyone. The test includes measures of cognitive function as well as neuromuscular function. The test is brief—it takes only about one to two minutes. It requires minimal explanation and no previous training for the subject to perform the test. The test allows for unique identification of the subject. The variables that are measured include some that have not been used previously (eg. mean and standard deviation of blink latencies), as well as some that we have used in our earlier inventions and patents (eg. mean and standard deviation of AVRs for eyelids closing and reopening during blinks). The new test does not rely on measurements of the pupil or of saccadic eye movements that others have used in alternative tests of fitness for duty.

To determine the feasibility of the test of this invention as a measure of psychomotor performance, a sleep deprivation experiment was conducted on 10 volunteers as a brief test of fitness for duty. The performance of the test of this invention was compared with a previously validated measure of performance impairment, the Johns Test of Vigilance (JTV).

It was reasoned that if a person could not satisfactorily complete a simple performance test, they would be unlikely to be fit to perform other activities at work.

Ten healthy volunteers participated in the study which was conducted for 25 continuous hours over two consecutive days (10 am Day 1-10 am Day 2).

Participants performed a test each hour (total of 25 sessions). Every three hours, this test was followed by a JTV test (total of 9 sessions).

Multiple Regression statistical analyses were used to develop a Drowsiness Impairment Score that could predict performance errors in the JTV from ocular variables recorded during a test.

Determining the best predictors to use for the multiple regression was based on significance levels and magnitude of beta (b*) coefficients (relative contribution of each independent variable in the prediction of the dependent variable) for each predictor.

The combination of predictors was determined by the magnitude of the $R^2$ value (coefficient of multiple determination), which explains the proportion of the variation in the dependent variable explained by the regression model, and is a measure of the goodness-of-fit of the model.

The final combination of predictors is shown below in the multiple regression result performance (average percent errors) at each three hourly testing session over the study period of 25 hours.

To assess predictive ability of these scores, the algorithm was applied to all test sessions for each subject. Test scores were then used to create contingency tables to determine the positive and negative predictive values of the Drowsiness Impairment scores.

In order to determine whether a given score could predict JTV performance impairment immediately afterwards, thresholds were selected that were somewhat arbitrary.

JTV Impairment was defined as >5% errors (defined as Errors of Omission, EOOs)

In the test of this invention impairment was defined as Predicted Drowsiness Impairment scores>10.5

The score threshold was chosen conservatively as it was determined that the consequences of incorrectly predicting impaired performance (false positive) were greater than those of failing to detect lower levels of impairment (false negative). In making this determination, there is always going to be a trade-off between higher specificity (limiting the number of false positives) and high sensitivity (correctly detecting impaired performance).

The predictive ability of Drowsiness Impairment scores may also be assessed by calculating positive and negative predictive values. The positive predictive value indicates the proportion of people who fail the test (impaired performance) who are subsequently shown to be impaired by a different test that has been independently validated (JTV). The negative predictive value indicates the proportion of people who pass the impairment test (performance not impaired) who are subsequently shown to be not impaired by JTV performance. Of the two types of predictive values, it was considered more important that the tests should have high positive predictive value to avoid false positives (incorrectly predicting impairment in a person who is not impaired).

The contingency table 2 shows how well the algorithm can predict JTV performance impairment at the time.

TABLE 1

Regression Summary for Dependent Variable:
Percent JTV EOOs
R = .78109561 $R^2$ = .61011036 Adjusted $R^2$ = .58690264
F(5,84) = 26.289 p < .00000 Std. Error of estimate: 6.2413

| N = 90 | b* | Std. Err. of b* | b | Std. Err. of b | t(84) | p-value |
|---|---|---|---|---|---|---|
| Intercept | | | −17.0538 | 4.43878 | −3.84200 | 0.000236 |
| Blink Latency Mean1 | 0.231287 | 0.078818 | 76.1541 | 25.95167 | 2.93446 | 0.004307 |
| Pos AVR Std Dev1 | 0.460178 | 0.081082 | 60.4409 | 10.64950 | 5.67547 | 0.000000 |
| Neg IED (ms) Mean | −0.251152 | 0.100766 | −0.0398 | 0.01597 | −2.49243 | 0.014652 |
| Neg AVR Std Dev | 0.393500 | 0.100786 | 22.4676 | 5.75455 | 3.90432 | 0.000190 |
| Percent OptaGo Errors | 0.150925 | 0.074621 | 0.5867 | 0.29006 | 2.02255 | 0.046300 |

The $R^2$ value of 0.61 was considered a very satisfactory outcome for this regression. The algorithm is the resulting regression equation created with the b coefficients. This equation can be applied to any test session to compute a Drowsiness Impairment Score.

Figure 1:
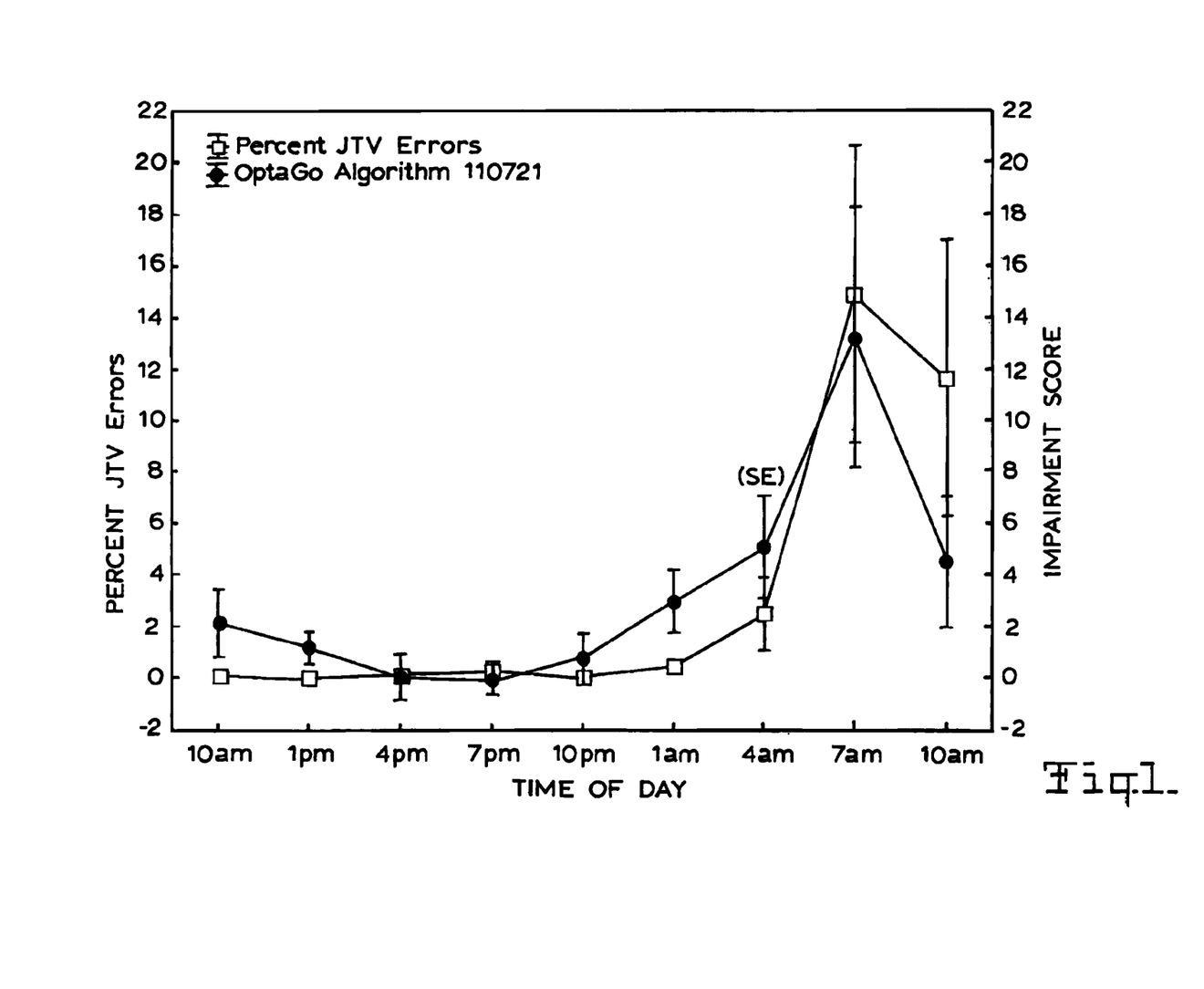
FIGS. 1-5 illustrate graphically the results of the method of this invention on sleep deprived subjects.
Figure 2:
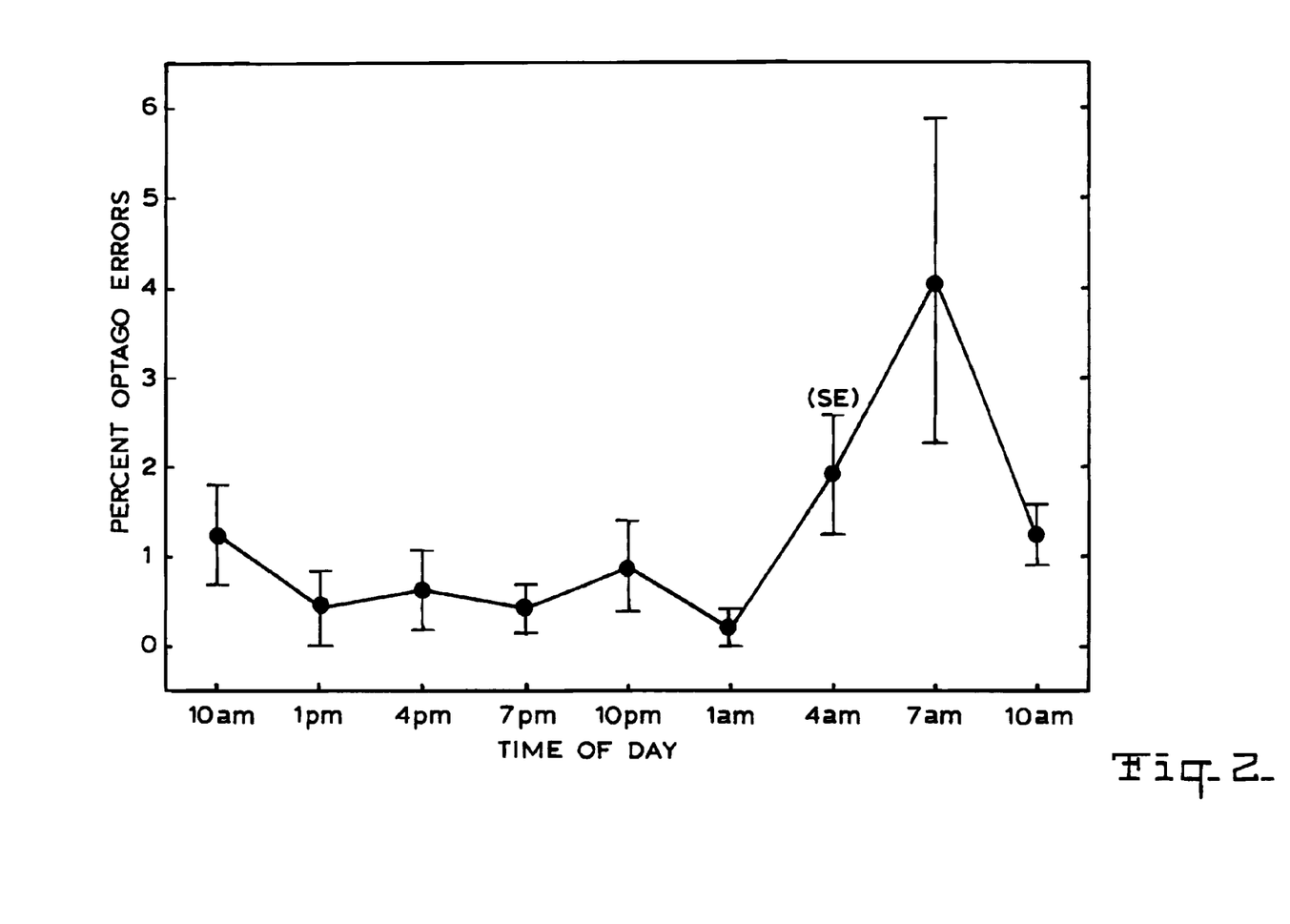
Figure 3:
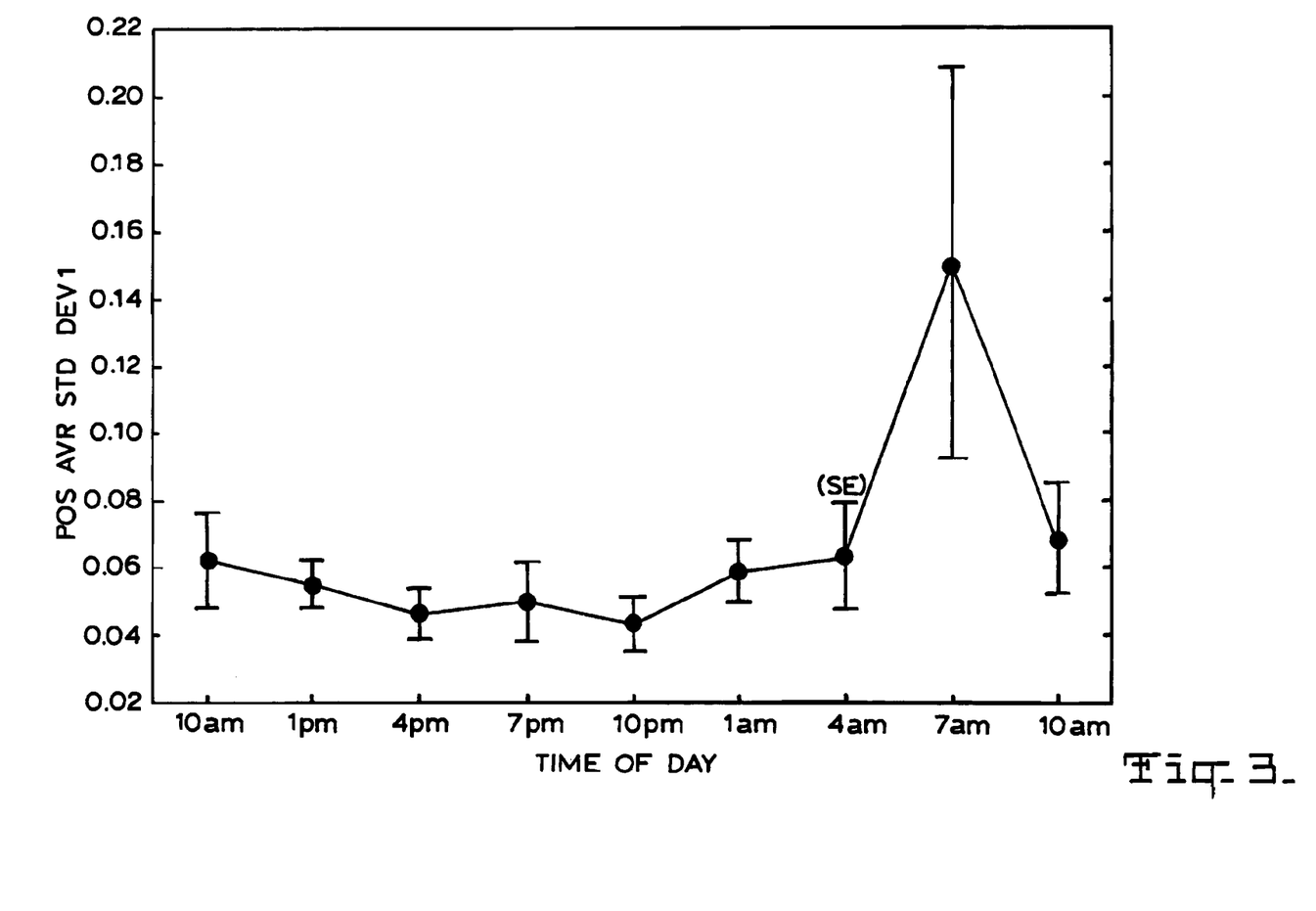
Figure 4:
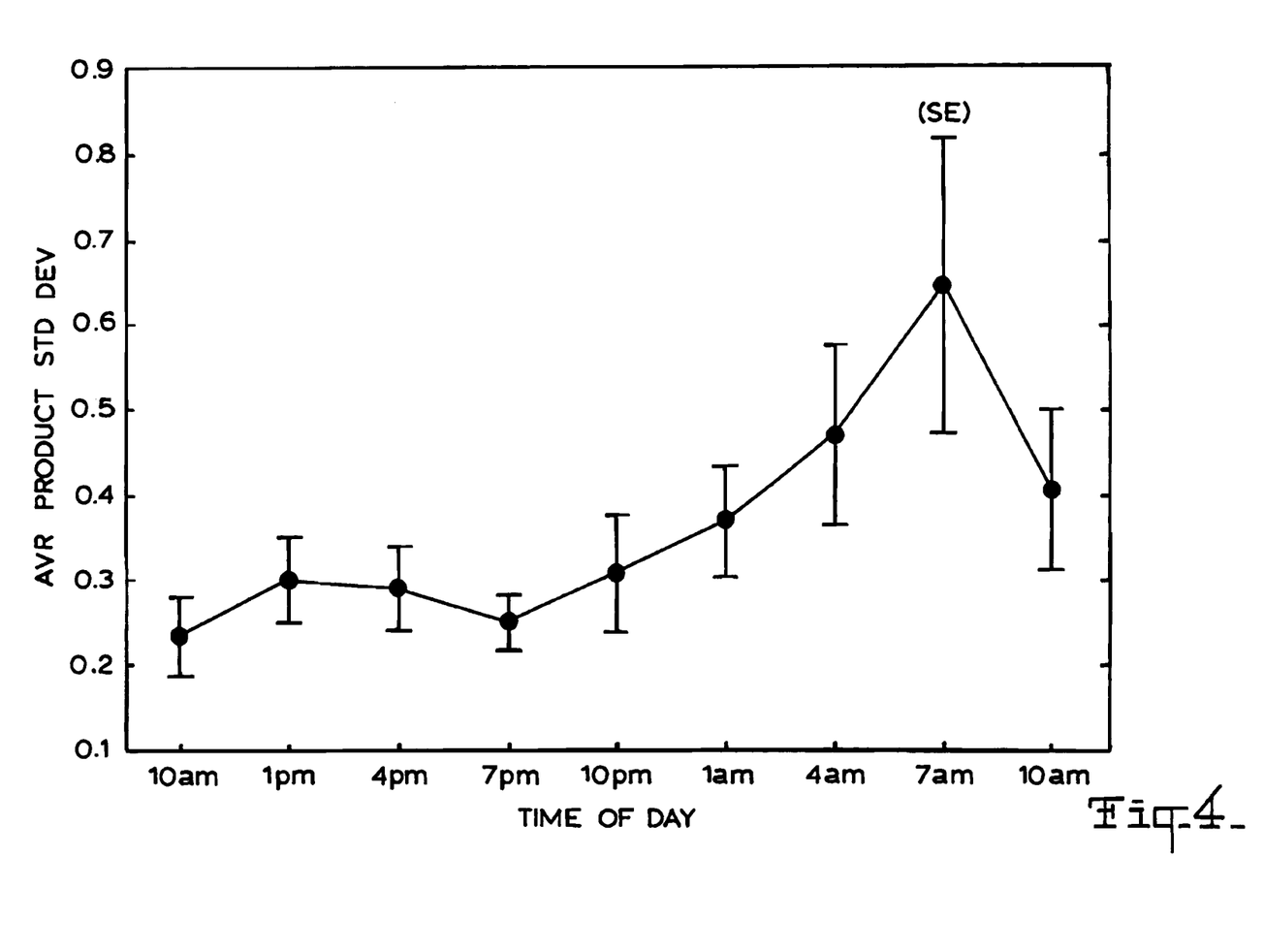
Figure 5:
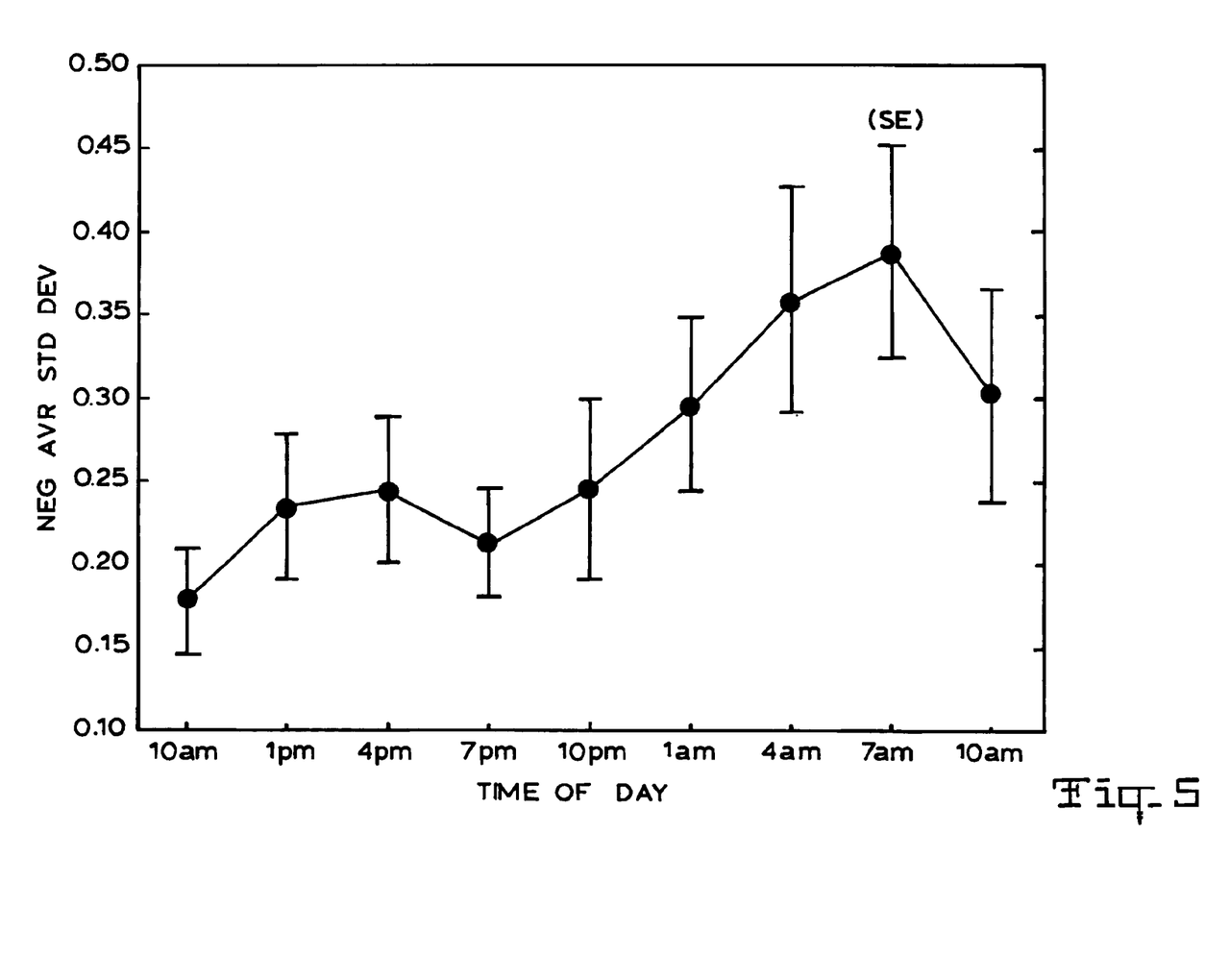

FIG. 1 shows average (+/− standard error) Drowsiness Impairment scores for 10 subjects and their subsequent JTV

TABLE 2

| N = 90 | JTV impaired | JTV not impaired |
|---|---|---|
| Impaired test performance (regression score ≥10.5) | 8 | 0 |

TABLE 2-continued

| N = 90 | JTV impaired | JTV not impaired |
|---|---|---|
| Not impaired test performance (regression score <10.5) | 6 | 76 |
| | 14 | 76 |

Positive Predictive Value=100% (People that fail test are impaired)

Negative Predictive Value=92.7% (People that pass test are not impaired)

The results suggest the test of this invention can measure performance impairment at the time with very high positive predictive value (100%) and high negative predictive value (92.7%). In other words, if an individual fails a test, it is almost certain that they will, in fact, be impaired at other tasks, i.e., they will be unfit for work at the time. Alternatively, if an individual passes the test, it is very likely that they will be fit for work. However, a small minority (7.3%) of these may subsequently prove to be unfit for work (false negative).

Performance impairment in the JTV varied with the normal circadian rhythm of alertness—drowsiness and the effects of overnight sleep deprivation. Impairment Scores for the test of this invention also varied with a strong circadian rhythm. Those skilled in the art will realise that this invention provides a unique and reliable test for assessing fitness for duty. Those skilled in the art will also realise that this invention may be carried out by embodiments other than those described without departing from the core teachings of this invention. The test method is applicable to testing for impairment due to alcohol and drugs such as cannabis, diazepam and other sedatives, as well as impairment due to sleep deprivation or particular sleep disorders such as obstructive sleep apnoea.

The invention claimed is:

1. A method of measuring concentration based fitness for duty of a user in advance of implementation of the duty based on voluntary blinks of the user, comprising:
    providing a source of visual stimulus;
    presenting from the source instances of brief visual stimuli separated by intervals of about 1.5-3 seconds;
    monitoring voluntary blinks in response to the brief visual stimuli; and
    determining the fitness for duty that measures impairment based on at least:
    measures of voluntary blink latency in response to the brief visual stimuli, the product of the amplitude to velocity ratio of eyelid closing and opening movements during voluntary blinking in response to the brief visual stimuli, the duration of voluntary blinks in response to the brief visual stimuli, and the failure to respond appropriately with a voluntary blink in response to each of the brief visual stimulus;
    assessing based on the measured fitness for duty whether the user is unfit to commence the duty.

2. The method as claimed in claim 1 in which determining is additionally based on 3 or more of:
    a) Mean Amplitude Velocity Ratio (AVR) of Eyelid Closure
    b) Standard Deviation Amplitude Velocity Ratio (AVR) of Eyelid Closure
    c) Mean Amplitude Velocity Ratio (AVR) of Eyelid Reopening
    d) Standard Deviation Amplitude Velocity Ratio (AVR) of Eyelid Reopening
    e) Mean Product of AVRs (Eyelid Closure×Eyelid Reopening)
    f) Standard Deviation Product of AVRs (Eyelid Closure× Eyelid Reopening)
    g) Mean Blink Latency
    h) Standard Deviation Blink Latency
    i) Percent Errors of Omission
    j) Percent Errors of Commission
    k) Percent Total Errors (Sum of Errors of Omission and Commission)
    l) Mean Blink Inter-Event Duration (time between maximum velocities of eyelid closure and eyelid reopening for each blink)
    m) Standard Deviation Blink Inter-Event Duration (time between maximum velocities of eyelid closure and eyelid reopening for each blink)
    n) Mean Total Blink Duration
    o) Standard Deviation Total Blink Duration
    p) Mean Eyelid Closure Duration
    q) Standard Deviation Eyelid Closure Duration
    r) The difference between a pair of percentiles for each variable.

3. The method of claim 1, wherein the determining is based on a failure to voluntarily blink within a predetermined time in response to at least one of the brief visual stimuli.

4. The method of claim 3, wherein determining is based on monitoring a voluntary blink in anticipation of at least one of the brief visual stimuli.

5. The method of claim 1, wherein the determining is based on monitoring a voluntarily blink in anticipation of at least one of the brief visual stimuli.

6. The method of claim 1, further comprising providing instructions, prior to the monitoring, to voluntarily blink in response to visual stimuli.

7. The method of claim 1, wherein the presenting from the source instances of visual stimuli separated by intervals of about 1.5-3 seconds is performed within a period of about 1-2 minutes.

8. The method of claim 1, wherein the determining fitness for duty is further based on measures of voluntary blink latency.

9. The method of claim 1, wherein the determining fitness for duty is further based on measures variability of eyelid movements during voluntary blinks in response to each of the brief visual stimulus.

* * * * *